US011549866B2

(12) United States Patent
Sercel et al.

(10) Patent No.: US 11,549,866 B2
(45) Date of Patent: Jan. 10, 2023

(54) SYSTEM AND METHOD FOR AUTOMATIC PLANT TISSUE SAMPLING

(71) Applicant: Fraunhofer USA, Inc., Plymouth, MI (US)

(72) Inventors: Patrick Sercel, Cambridge, MA (US); Aaron Sharpe, Medford, MA (US); Sudong Shu, Andover, MA (US); Holger Wirz, Medford, MA (US)

(73) Assignee: Fraunhofer USA, Inc., Plymouth, MI (US)

( * ) Notice: Subject to any disclaimer, the term of this patent is extended or adjusted under 35 U.S.C. 154(b) by 205 days.

(21) Appl. No.: 16/990,799

(22) Filed: Aug. 11, 2020

(65) Prior Publication Data

US 2021/0025788 A1 Jan. 28, 2021

Related U.S. Application Data

(62) Division of application No. 14/443,056, filed as application No. PCT/US2013/071929 on Nov. 26, 2013, now Pat. No. 10,830,671.

(Continued)

(51) Int. Cl.
*G01N 1/04* (2006.01)
*G01N 35/00* (2006.01)
(Continued)

(52) U.S. Cl.
CPC .............. *G01N 1/04* (2013.01); *C12M 33/00* (2013.01); *C12M 41/48* (2013.01); *G01N 35/00732* (2013.01); *G01N 2001/045* (2013.01)

(58) Field of Classification Search
CPC ... G01N 1/04; G01N 35/00732; C12M 33/00; C12M 41/48
See application file for complete search history.

(56) References Cited

U.S. PATENT DOCUMENTS

| 4,854,802 A | 8/1989 | deGroot |
| 5,382,268 A | 1/1995 | Brown et al. |

(Continued)

FOREIGN PATENT DOCUMENTS

| CN | 1073887 | 7/1993 |
| CN | 1908810 | 2/2007 |

(Continued)

OTHER PUBLICATIONS

Lenk et al., "Multispectral fluorescence and reflectance imaging at the leaf level and its possible applications," J Exper Bot 58(4):807-814, 2006.

(Continued)

*Primary Examiner* — Tarun Sinha
(74) *Attorney, Agent, or Firm* — Dentons US LLP; David Lanzotti

(57) ABSTRACT

An automatic plant tissue sampler and a method for operating the same are provided. The sampler can include a plant handler configured to transport a plurality of plants to an imager. The imager may be configured to image plants to identify a sampling location. The automatic plant tissue sampler also includes a sampler configured to remove a tissue sample from the sampling location of plants, and a collection vessel configured to receive the tissue samples. The automatic plant tissue sampler may transport a plurality of plants to an imager and images the plurality of plants to identify a sampling location. The automatic plant tissue sampler can remove a tissue sample from the sampling location of the plurality of plants and store the tissue samples in a collection vessel for testing.

10 Claims, 7 Drawing Sheets

Related U.S. Application Data

(60) Provisional application No. 61/729,956, filed on Nov. 26, 2012.

(51) Int. Cl.
    *C12M 1/36*     (2006.01)
    *C12M 1/26*     (2006.01)

(56) References Cited

U.S. PATENT DOCUMENTS

| | | | |
|---|---|---|---|
| 5,439,490 | A | 8/1995 | Janus |
| 6,172,328 | B1 | 1/2001 | Jones et al. |
| 7,506,472 | B2 | 3/2009 | Leyns et al. |
| 2004/0029213 | A1 | 2/2004 | Callahan et al. |
| 2007/0207485 | A1 | 9/2007 | Deppermann et al. |
| 2009/0042180 | A1 | 2/2009 | Lafferty |
| 2009/0061449 | A1 | 3/2009 | Osborn et al. |
| 2009/0077932 | A1 | 3/2009 | Cope |
| 2009/0139353 | A1 | 6/2009 | Kline |
| 2009/0178159 | A1 | 7/2009 | Taramino et al. |
| 2009/0188332 | A1* | 7/2009 | Actis .............. G01N 1/286 73/864.31 |
| 2010/0044356 | A1* | 2/2010 | Cope ............... B23K 26/0876 219/121.67 |
| 2010/0248370 | A1 | 9/2010 | Moynahan |
| 2011/0197981 | A1* | 8/2011 | Visser ............. G08B 21/0211 73/865.8 |
| 2012/0288854 | A1 | 11/2012 | Depperman et al. |

FOREIGN PATENT DOCUMENTS

| | | |
|---|---|---|
| CN | 101659921 A | 3/2010 |
| EP | 2175279 | 4/2010 |
| WO | 9203913 A1 | 3/1992 |
| WO | 0142796 A1 | 6/2001 |
| WO | 2012012411 A2 | 1/2012 |

OTHER PUBLICATIONS

Alenya et al., "3D modelling of leaves from color and ToF data for robotized plant measuring," IEEE International Conference on Robotics and Automation (ICRA), pp. 3408-3414, May 9, 2011.

International Search Report for PCT/US13/71929, dated Apr. 18, 2014.

European Search Report for EP Application No. 13857169.0, dated Jun. 8, 2016.

Leica Microsystems, "Laser Microdissection in Plant Research," 3 pages, BIOspectrum Jun. 2006, Elsevier GmbH, Dec. 2006, Heidelberg, Germany.

Lenk, Sandor et al., "Multispectral fluorescence and reflectance imaging at the leaf level and its possible applications," Journal of Experimental Botany, vol. 58 (4), pp. 807-817, May 21, 2006, Oxford University Press.

Alenya, G. et al., "3D modeling of leaves from color and ToF data for robotized plant measuring," pp. 3408-3414, 2011 IEEE International Conference on Robotics and Automation, Shanghai International Conference Center, May 9-13, 2011, Shanghai, China.

Alenya, Guillem et al., "Robotized plant probing," p. 12, 2nd International Plant Phenotyping Symposium 2011, Sep. 5-7, 2011, Julich, Germany.

Day et al., "Be more specific! Laser-assisted microdissection of plant cells," Trends in Plant Science, 10(8) Aug. 2005.

Ramsay et al., "Laser capture microdissection: a novel approach to microanalysis of plant-microbe interactions," Molecular Plant Pathology, 7(5): 429-435, 2006.

Notice of Opposition regarding Europe Patent No. 292243 dated Dec. 3, 2019.

* cited by examiner

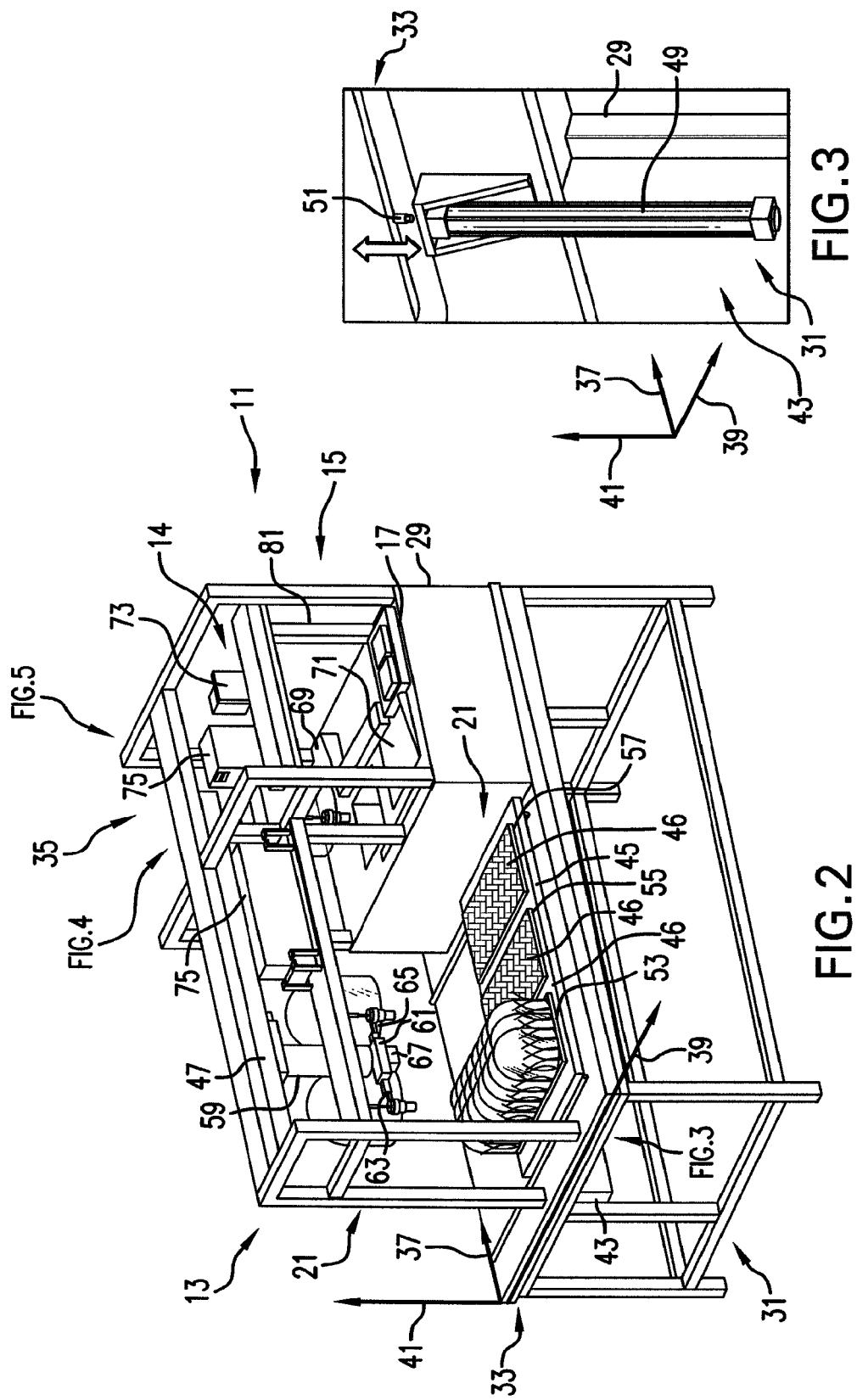

SYSTEM AND METHOD FOR AUTOMATIC PLANT TISSUE SAMPLING

CROSS REFERENCE TO RELATED APPLICATIONS

This application is a divisional of application U.S. application Ser. No. 14/443,056, filed May 14, 2015, which is a 371 National Stage Entry of PCT/US2013/071929, filed Nov. 26, 2013, which claims benefit of U.S. provisional application No. 61/729,956, filed Nov. 26, 2012, incorporated herein by reference in their entirety.

FIELD OF THE INVENTION

The invention relates generally to plant genetic testing. In particular, the invention relates to a system, method, and apparatus to automatically sample plant tissue.

DESCRIPTION OF RELATED ART

Development of novel, desirable plant germplasm begins with the analysis and definition of problems and weaknesses of the current germplasm, the establishment of program goals, and the definition of specific breeding objectives. The goal is to combine in a single variety beneficiary combinations of desirable traits from parental germplasm. Development of such combinations may be assisted by testing of the developing germplasm. Some tests require removal of a tissue sample from the germplasm to conduct the test. Procurement of tissue samples for these tests has typically been conducted in a time-consuming manual process. The time-consuming nature of the testing is underscored by the large sample sizes often involved.

SUMMARY

Problems in the prior art are generally solved or circumvented, and technical advantages are generally achieved, by embodiments that provide a system, method, and apparatus to automatically sample plant tissue as follows.

According to an illustrative embodiment, an automatic plant tissue sampling system is described. The system includes a plant handler configured to transport one or more plants from a first location to a second location, and an imager configured to image a plant moved by the plant handler to identify a sampling location. The system also includes a processor in communication with the imager and configured to receive an image of the plant and further configured to select a location on the plant to sample. The system further includes a sampler configured to remove a tissue sample from the sampling location of the plant selected by the processor, and a collection vessel configured to receive tissue samples.

In some embodiments, the plant handler is configured to transport the plant from the imager after removal of a tissue sample.

In some embodiments, the plant handler includes a scanner configured to read an identifier associated with the plant, and the collection vessel associates the tissue sample with the identifier of the sampled plant.

In some embodiments, the scanner is a bar code scanner and the identifier is a bar code. In another embodiment, the automatic plant tissue sampling system further includes a control system configured to store the location of the tissue sample in the collection vessel in a memory location associated with the bar code of the sampled plant.

In some embodiments, the imager is configured to determine the sampling locations based on at least one of a size, shape, or color of plants being sampled, or a portion thereof.

In some embodiments, the sample location is a green portion of a leaf.

In some embodiments, the sample location is a rectangular shaped portion of a leaf.

In some embodiments, the sample location is a leaf having a length of about 6 mm and width of about 12 mm.

In some embodiments, the imager includes a camera.

In some embodiments, the camera includes an infrared camera, an ultraviolet camera, or a visible light camera.

In some embodiments, the sampling location includes a leaf.

In some embodiments, the sampler includes a laser cutter.

In some embodiments, the laser cutter is guided to the sampling location in response to an image produced by the imager.

In some embodiments, the collection vessel maintains the tissue samples for testing.

In some embodiments, the collection vessel includes a microtiter configured to receive the tissue sample and associate the tissue sample with the sampled plant.

In some embodiments, the system includes automatic controls communicatively coupled to the plant handler, the imager, and the sampler for operation thereof.

In some embodiments, the processor is in communication with the plant handler and configured to move the plant to the imager.

In some embodiments, the collection vessel is further configured to store the tissue sample for testing.

According to another illustrative embodiment, a method for sampling plant tissue is described. The method transports one or more plants from a first location to a second location with a plant handler, the second location proximate to an imager. The method images a plant with an imager to identify a sampling location, and removes a tissue sample from the sampling location of the plant with a sampler. The method stores the tissue sample in a collection vessel. At least the step of imaging a plant and the step of removing a tissue sample are automated.

In some embodiments, the step of imaging a plant includes identifying at least one of a size, shape, or color of a plurality of plants.

In some embodiments, the method includes identifying the sampling location based on at least one of a size, shape, or color of a plurality of plants.

In some embodiments, the step of imaging the plant includes using a visible light camera, an infrared camera, or an ultraviolet camera to generate an image.

In some embodiments, the step of transporting one or more plants from a first location to a second location includes reading an identifier associated with each plant with a scanner at the first location and transporting the scanned plant to the second location.

In some embodiments, the step of storing the tissue samples in a collection vessel includes associating the tissue samples with an identifier of the sampled plant.

In some embodiments, the identifier is a bar code, and the method reads the bar code with a bar code scanner and stores the location of the tissue sample in the collection vessel in a memory location associated with the bar code.

In some embodiments, the method includes transporting the one or more plants from the imager after removal of a tissue sample.

In some embodiments, the step of removing a tissue sample from the sampling location of the plant includes removing a tissue sample from a leaf of the plant.

In some embodiments, the step of removing a tissue sample from the sampling location of the plant includes removing the tissue sample with a laser cutter.

In some embodiments, the method further includes guiding the laser cutter to the sampling location in response to an image produced by the imager.

In some embodiments, the step of storing the tissue samples in a collection vessel includes maintaining the tissue samples in the collection vessel for testing.

In still another illustrative embodiment, an automatic plant sampling system for automatically sampling plant tissue of an individual plant selected from a group of one or more plants collectively conveyed to the automatic plant sampling system is described. The automatic plant sampling system includes a frame assembly having a first axis, a second axis orthogonal to the first axis, and a third axis orthogonal to the first axis and the second axis. The system also includes a plant handling system coupled to the frame assembly so that a portion of the plant handling system moves relative to the frame assembly. The plant handling system is configured to select the individual plant from the one or more plants, transport the individual plant to a sampling system for sampling, and transport the individual plant from the sampling system to a post sampling location. The sampling system is coupled to the frame assembly proximate to the plant handling system and configured to determine a suitable sampling location of the individual plant, sample a portion of plant tissue from the sampling location to create a tissue sample, and transport the tissue sample to a storage system. The storage system can be coupled to the frame assembly proximate to the sampling system and configured to associate the tissue sample with the individual plant and maintain the tissue sample in a suitable condition for testing. The system further includes a controls system communicatively coupled to the plant handling system, the sampling system, and the storage system. The controls system is automatically operable to coordinate movement and operation of the plant handling system, the sampling system, and the storage system for sampling of the individual plant.

In some embodiments, the plant handling system further includes a plug handler mechanically coupled to the frame assembly. The plug handler is configured to move parallel to the first axis between the one or more plants and the sampling system. The plug handler is further configured to identify the individual plant of the one or more plants and secure the individual plant for movement relative to the one or more plants. The system also includes a tray table mechanically coupled to the frame assembly. The tray table is configured to collectively receive the one or more plants and move relative to the frame assembly parallel to the second axis. The system also includes a popper mechanically coupled to the frame assembly and configured to move relative to the frame assembly parallel to the first axis and the third axis. The tray table receives the one or more plants and the controls system operates to move the tray table, the popper, and the plug handler to move each device proximate to the individual plant of the one or more plants. The popper engages the individual plant to move the plant along the third axis into the plug handler, and the plug handler secures the individual plant and moves along the first axis to transport the individual plant to the sampling system.

In some embodiments, the tray table is coupled to a medial portion of the frame assembly; the plug handler is coupled to an upper portion of the frame assembly, the upper portion being above the medial portion; and the popper is coupled to a lower portion of the frame assembly, the lower portion being below the medial portion. The tray table may have a plurality of openings. Each opening contains a respective plant of the one or more plants, and the popper is configured to engage each plant from below the tray table through each respective opening of the plurality of openings.

In some embodiments, the plug handler includes a plug handler head coupled to an end of the plug handler proximate to the tray table, and a gripper mounted to the plug handler head and configured to selectively grip the individual plant. The plug handler head may also include an identification device coupled to the plug handler head and configured to identify the individual plant when the plug handler head is proximate to the individual plant.

In some embodiments, each plant of the one or more plants is labeled with a bar code and the plant identification device is a bar code scanner configured to scan the bar code positioned on each individual plant of the one or more plants.

In some embodiments, each plant of the one or more plants is labeled with a radio frequency identification (RFID) tag and the plant identification device is an RFID scanner configured to scan the RFID tag positioned on each individual plant of the one or more plants.

In some embodiments, the gripper is a first gripper and the plug handler further includes the first gripper extending outwardly from the plug handler head in a first direction parallel to the first axis, and a second gripper coupled to the plug handler head and extending outwardly from the plug handler head in a second direction parallel to the first axis and opposite the first direction. The identification device is positioned between the first gripper and the second gripper, and the first gripper and the second gripper are configured to grip and hold separate plants of the one or more plants. The plug handler head is rotatable so that the first gripper and the second gripper selectively occupy opposite locations on the first axis.

In some embodiments, the sampling system includes a plant positioner coupled to the frame assembly and configured to receive the individual plant from the plant handling system, and a chuck coupled to the frame assembly proximate to the plant positioner. The chuck is configured to secure a portion of the individual plant for sampling. The sampling system also includes an imager coupled to the frame assembly proximate to the chuck. The imager is configured to determine one or more of the color, shape, and size of the individual plant. The plant positioner is further configured to manipulate the individual plant to allow the imager to determine one or more of the color, shape, and size of the individual plant and determine the sampling location in response. The plant positioner positions the individual plant to align the sampling location with the chuck. The sampling system also includes a sampler coupled to the frame assembly proximate to the chuck. The sampler is configured to remove a tissue sample from the sampling location. The sampling system still further includes a sample transport system coupled to the frame assembly proximate to the chuck that is configured to retrieve the tissue sample of the individual plant from the chuck and transport the sample portion to the storage system. The controls system is communicatively coupled to the plant positioner, the chuck, the imager, the sampler, and the sample transport system to control and operate the plant positioner to receive the individual plant from the plant handling system, manipulate the individual plant for identification by the imager, and position the plant so that the sample location is proximate to the chuck. The controls system is further configured to operate the chuck to secure the sample location to the chuck, to operate the sampler to remove the tissue sample from the sampling location, and to operate the sample transport system to transport the tissue sample to the storage system.

In some embodiments, the plant positioner is a motorized rotary gripper configured to grip and rotate the individual plant.

In some embodiments, the plant positioner moves parallel to the second axis.

In some embodiments, the chuck is a vacuum chuck configured to supply an air pressure at a location proximate to a surface of the chuck, wherein when the plant positioner brings the sampling location proximate to the chuck, the pressure draws the sample location to the chuck.

In some embodiments, the pressure flattens a portion of the sample location.

In some embodiments, the pressure is a pressure less than an ambient pressure at the automatic plant sampling system.

In some embodiments, the pressure is a pressure greater than an ambient pressure at the automatic plant sampling system.

In some embodiments, the imager is an imaging system having at least one camera.

In some embodiments, the sampler is a laser cutting device operable in response to the image of the individual plant generated by the imaging system.

In some embodiments, the sampler is a laser cutting device.

In some embodiments, the sampler is a device having a plurality of knives configured to cut the tissue sample from the sample location.

In some embodiments, the sampler is a tissue squeezing device configured to apply compressive pressure to remove the tissue sample from the sample location.

In some embodiments, the tissue squeezing device is a hole punching device.

In some embodiments, the sample transport system applies an air pressure less than the ambient pressure of the automatic plant sampling system to draw the tissue sample to a carrier for transportation to the storage system.

In some embodiments, the storage system includes a microtiter having a plurality of isolated locations. Each location has a scannable label associated with the individual plant. The storage system also includes a cooling system positioned proximate to the microtiter and configured to maintain the microtiter at a pre-determined temperature.

In some embodiments, the cooling system is dry ice disposed adjacent to an exterior of the microtiter.

In yet another illustrative embodiment, an apparatus for selecting, sampling, and storing a tissue sample from an individual plant of a group of one or more plants is described. The apparatus includes a frame assembly having a first axis, a second axis orthogonal to the first axis, and a third axis orthogonal to the first axis and the second axis. The apparatus also includes a plant handler mounted to the frame assembly that has a plurality of grippers to manipulate the individual plant of the one or more plants to collect a tissue sample of the individual plant. The apparatus also includes a sampler mounted to the frame assembly that has a sample identifier and a tissue sample collection device to identify, collect, and store the tissue sample of the individual plant. The plant handler is configured to orient the plant within the sampler. The apparatus also includes a controls system communicatively coupled to the plant handler and the sampler. The controls system is configured to coordinate movement and operation of the plant handler and the sampler.

In some embodiments, the plant handler includes a plug handler having one or more of the plurality of grippers. The plug handler is mechanically coupled to the frame assembly and is configured to move parallel to the first axis between the one or more plants and the sampler. The plug handler is further configured to identify the individual plant of the one or more plants and grip the individual plant with one or more of the plurality of grippers for movement of the individual plant relative to the one or more plants. The plant handler includes a tray table mechanically coupled to the frame assembly. The tray table is configured to collectively receive the one or more plants and move relative to the frame assembly parallel to the second axis. The plant handler also includes a popper mechanically coupled to the frame assembly and configured to move relative to the frame assembly parallel to the first axis and the third axis. The tray table receives the one or more plants and the controls system operates to move the tray table, the popper, and the plug handler proximate to the individual plant of the one or more plants. The popper engages the individual plant to move the plant along the third axis into a gripper of the plurality of grippers, which grips the individual plant and moves along the first axis to transport the individual plant to the sampler.

In some embodiments, the plug handler also includes a plug handler head coupled to an end of the plug handler proximate to the tray table. The one or more grippers are mounted to the plug handler head, and the plug handler head is rotatable to selectively position each gripper of the plurality of grippers in a plan containing the first axis. The plug handler also includes an identification device coupled to the plug handler head and configured to identify the individual plant.

In some embodiments, each plant of the one or more plants is labeled with a bar code and the plant identification device is a bar code scanner configured to scan the bar code positioned on each individual plant of the one or more plants.

In some embodiments, each plant of the one or more plants is labeled with a radio frequency identification (RFID) tag and the plant identification device is an RFID scanner configured to scan the RFID tag positioned on each individual plant of the one or more plants.

In some embodiments, the apparatus further includes a plant positioner having a motorized rotary gripper coupled to the frame assembly. The plant positioner is configured to move parallel to the second axis and receive the individual plant from the plant handler. The apparatus also includes a chuck coupled to the frame assembly proximate to the plant positioner. The chuck is configured to engage a portion of the individual plant for sampling. The sampler includes an imager coupled to the frame assembly proximate to the chuck. The imager is configured to determine one or more of the color, shape, and size of the individual plant. The sampler also includes a cutter coupled to the frame assembly proximate to the chuck. The cutter is configured to remove a tissue sample from the sampling location of the individual plant. The sampler also includes a tissue sample transporter (TST) coupled to the frame assembly proximate to the chuck that is configured to retrieve the tissue sample of the individual plant from the chuck and transport the tissue sample to a storage assembly. The plant positioner is further configured to manipulate the individual plant to allow the imager to determine one or more of the color, shape, and size of the individual plant and determine the sampling location.

The plant positioner positions the individual plant to align the sampling location with the chuck. The controls system is communicatively coupled to the plant positioner, the chuck, the imager, the cutter, and the tissue sample transporter to control and operate the plant positioner to manipulate the individual plant for identification by the imager and position the plant so that the sample location is proximate to the chuck. The control system is further configured to operate the chuck to secure the sample location to the chuck, operate the sampler to remove the tissue sample from the sampling location, and operate the tissue sample transporter to transport the tissue sample to the storage assembly.

In some embodiments, the chuck is a vacuum chuck configured to supply a pressure less than an ambient pressure at a location proximate to a surface of the chuck. When the plant positioner brings the sampling location proximate to the chuck, the pressure draws the sample location to the chuck.

In some embodiments, the pressure flattens a portion of the sample location.

In some embodiments, the imager is an imaging system having at least one camera.

In some embodiments, the sampler is a laser cutting device.

In some embodiments, the sampler is a device having a plurality of knives configured to cut the tissue sample from the sample location.

In some embodiments, the sampler is a hole punching device configured to apply compressive pressure to remove the tissue sample from the sample location.

In some embodiments, the collection vessel includes a microtiter having a plurality of isolated locations each location having a scannable label associated with the individual plant, and a dry ice receptacle for placing dry ice proximate to the microtiter to maintain the microtiter at a pre-determined temperature.

In another illustrative embodiment, a method for automatically sampling individual plants from a group of one or more plants is described. The method loads flats containing a plurality of plants into an automatic sampling device having a plant handling system and a plant sampling system. Each plant has a unique identifier. The method selects an individual plant from the tray and secures the individual plant in the plant handling system. The method moves the individual plant with the plant handling system to the plant sampling system, and secures the individual plant with the plant sampling system. The method releases the individual plant with the plant handling system. The method identifies at least one of a color, size, and shape of the individual plant with the plant sampling system, and determines a sampling location of the individual plant based on at least one of the color, size, and shape of the individual plant. The method secures the individual plant for sampling with the plant sampling system, and isolates a tissue sample from the individual plant with the plant sampling system. The method transports the tissue sample to a collection vessel with the plant sampling system and associates the tissue sample with the identifier of the individual plant. The method stores the tissue sample for testing and returns the individual plant for further cultivation with the plant handling system.

In some embodiments, the method engages the individual plant with a popper of the plant handling system to move the individual plant from a tray table of the plant handling system into a gripper of the plant handling system.

In some embodiments, the method images the individual plant with an imaging system of the plant sampling system.

In some embodiments, to the determine shape, size, and color of the individual plant, the method selects the sampling location based on a predetermined size, color, and shape that corresponds with desired characteristics.

In some embodiments, the desired characteristics include a size, color, and shape associated with an increased likelihood of plant survival.

In some embodiments, the method orients the individual plant so that the sample location is proximate to a chuck of the plant sampling system. The method positions the sample location with the chuck so that the sample location is disposed for isolating, and inhibits movement of the sample location with the chuck.

In some embodiments, the method applies a pressure lower than an ambient pressure of the plant sampling system to draw the sample location to the chuck.

In some embodiments, the method cuts the sample location with a laser cutting apparatus to remove the tissue sample from the individual plant.

In some embodiments, the method collects the tissue sample with a vacuum system and carries the tissue sample to a tissue sample collection plate associated with the individual plant.

In some embodiments, the method repeats until each individual plant of the plurality of plants is sampled.

BRIEF DESCRIPTION OF THE DRAWINGS

Illustrative embodiments are described in detail below with reference to the attached drawing figures, which are incorporated by reference herein, and wherein:

FIG. 2 illustrates a schematic perspective view of an illustrative automatic plant tissue sampler;

FIG. 3 illustrates a schematic detail view of an illustrative popper of the automatic plant tissue sampler of FIG. 2;

DETAILED DESCRIPTION OF THE INVENTION

The invention allows for the automated and high-throughput sampling of plant tissue, representing a significant advance over the prior art. The processes provided herein increase the speed of tissue sampling while decreasing the error rate associated with prior art processes that relied on manual sampling. In addition, the processes provided herein allow for tissue sampling of plants at an earlier post-germination stage of plant cultivation. Still further, the processes provided herein may fully automate the tissue sampling process while leaving each sampled plant within a growth medium, allowing continued cultivation of the plant following tissue sampling. For example, the system provided herein may sample a high volume of samples in a short time while improving consistency of the samples and accuracy of association of the samples with the plant from which the sample was selected. The process as provided may be applied to sampling of tissues from any plant species to provide tissue samples for analytical testing that could involve DNA, RNA, protein, or any other analytical tests. The disclosed embodiments can be used on transgenic tissue culture regenerants (R0 plants) or subsequent generations of transgenic plants (R1 and beyond). The disclosed embodiments can also be used to collect samples from non-transgenic plants, for example, for the purposes of performing molecular marker analysis in the context of molecular breeding programs. Other uses could include testing for metabolites in chemical screens or physiological assays. The exemplary embodiments also provide a flexible process that incorporates input and output. The exemplary embodiments also provide, in certain aspects, for delivering plant tissues for sampling. In one embodiment, this includes vacuum-assisted positioning and flattening of leaf or other plant tissues to facilitate sampling. Still further, the exemplary embodiments provide a non-contact laser cutting system that reduces cross contamination of tissue samples. In addition, the disclosed embodiments may accommodate a larger range of plant sizes. The disclosed embodiments also provide repeatable sample size and quality of tissue samples through the use of automatically controlled imaging and cutting of plant tissue. In a exemplary embodiment, the process may select and process each tissue sample in as little as 10 seconds.

Figure 1:
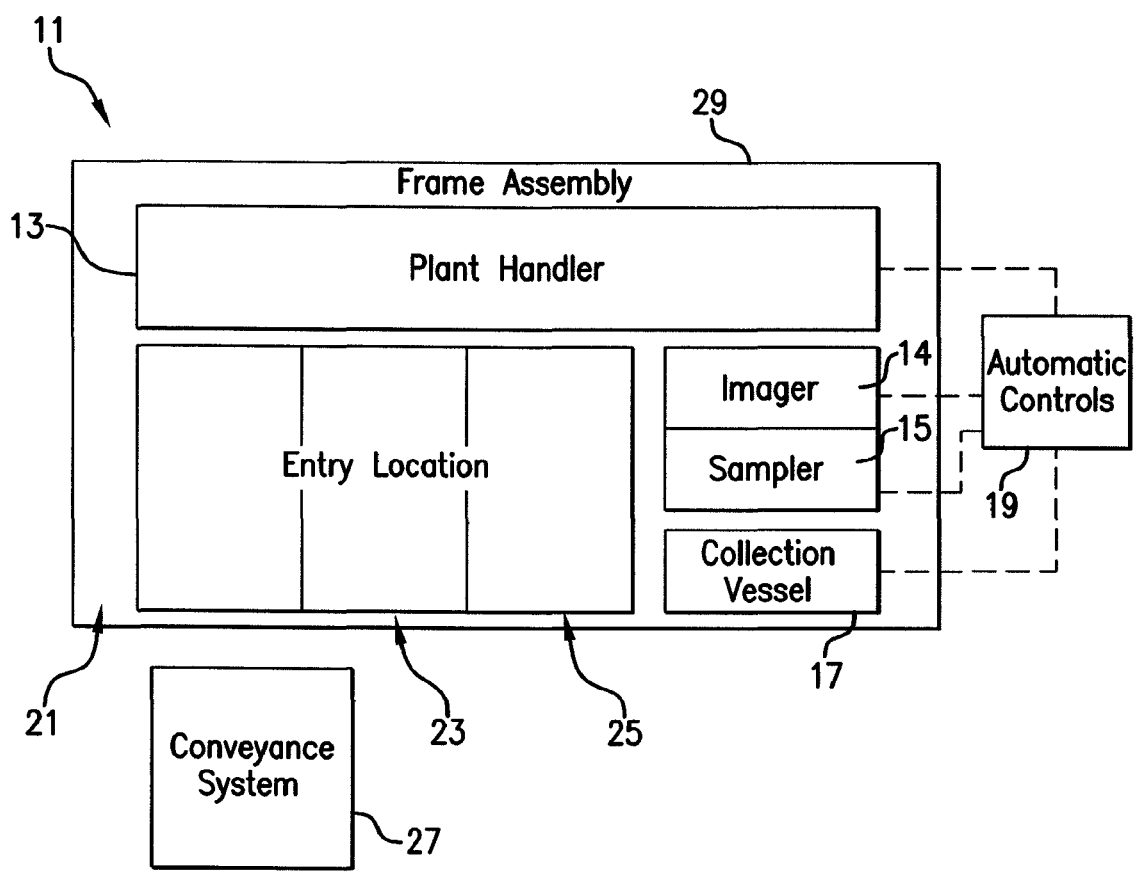
FIG. 1 illustrates a schematic diagram of an illustrative system for automatic plant tissue sampling.

FIG. 1 schematically illustrates an illustrative automatic plant tissue sampling system (APTSS) 11. As shown in FIG. 1, the illustrative APTSS 11 includes, in one embodiment, a plant handler 13, an imager 14, a plant sampler 15, a collection vessel 17, and automatic controls 19. Generally, the plant handler 13 may be a mechanical assembly having one more apparatuses configured to transport a plant to the sampler 15 from a group of plants placed proximate to the APTSS 11. The imager 14 includes one or more apparatuses configured to identify a suitable sampling location of the plant. The sampler 15 includes, for example, one or more components configured to take a tissue sample from the sampling location of the plant and transport the tissue sample to the collection vessel 17. In one exemplary embodiment, the sampler 15 includes a vacuum chuck, described in more detail below, configured to secure the plant for tissue sampling without damaging the plant. The collection vessel 17, for example, includes one or more components configured to store the tissue samples in a manner that allows for testing of the tissue samples at a desired time. The automatic controls 19 include, in one embodiment, suitable control equipment configured to operate the plant handler 13, the imager 14, the sampler 15, and the collection vessel 17. In the illustrated embodiment, the automatic controls 19, which may include one or more computer processors and communication electronics, are communicatively coupled to the plant handler 13, the imager 14, the sampler 15, and the collection vessel 17 for transmission of operative signals between the automatic controls 19 and the plant handler 13, the imager 14, the sampler 15, and the collection vessel 17 for operation thereof.

A plurality of plants may be brought to the APTSS 11 at a general entry location 21, a location of the APTSS 11 where the plant handler 13 may access the plurality of plants. In some exemplary embodiments, the plurality of plants are conveyed to the entry location 21 of the APTSS 11 by an operator or other laborer. The operator or laborer may, for example, assemble the plurality of plants onto a flat or other member and physically convey the plants to the entry location 21 of the APTSS 11. As used herein, "flat" refers to any object or device suitable for holding, supporting, arranging or otherwise carrying or moving one or more given sample(s), such as plants or other sources of tissue to be sampled in accordance with the invention.

In other exemplary embodiments, a plurality of plants are conveyed to the APTSS 11 by an automatic conveyance system 27 that may deposit the plurality of plants with the APTSS 11 in any suitable manner. In a non-limiting example, the conveyance system 27 may receive the plurality of plants at a separate location and convey the plurality of plants along a conveyor, such as a conveyor belt or any other suitable motorized apparatus. The plants may be hand-assembled by an operator and placed onto the conveyor assembly. In other embodiments, the plants may be automatically assembled and conveyed on the conveyance system 27. As used herein, assembly of the plants refers to the grouping of more than one plant into a batch or flat to be processed by the APTSS 11.

The plant handler 13, in one embodiment, selects a plant from the plurality of plants at the entry location 21 and moves the plant from the plurality of plants to the imager 14. In an exemplary embodiment, the plant handler 13 includes an overhead gantry apparatus having a mechanical gripping device configured to pick up a plant from the plurality of plants and move the plant to the imager 14. In another exemplary embodiment, the plant handler 13 may include an apparatus configured to place a plant on a conveyor that may move the plant to the imager 14. Alternative configurations of the plant handler 13 to move the plant to the imager 14 may be utilized. There, the imager 14 images the plant and identifies a suitable sampling location. The imager 14 may also or alternatively include an ultraviolet camera, an infrared camera, or any other suitable imaging device. The imager 14 may utilize one or more components, operate in one or more frequency spectrums, and have resolution that provides accuracy in accordance with the principles of the present invention. For example, the imager 14 may include a visible light camera configured to image the plant to determine the suitable sampling location. In one exemplary embodiment, the plant may be a corn plant, or any other species, and the imager 14 may image the leaf. The automatic controls 19 may then determine that the leaf is an appropriate size or shape, for example, larger than 6 mm by 12 mm rectangle, have a suitable hue, for example, have a green hue, be of a suitable shape, for example, substantially rectangular, or some combination thereof. The plant sampler 15 then removes a tissue sample from the sampling location and transports the tissue sample to, for example, the collection vessel 17. In one exemplary embodiment, the plant sampler 15 may be a laser cutting device, a mechanical apparatus having a plurality of knives, a hole-punching device, or any other device configured to remove a tissue sample from a plant without destroying the plant. A person skilled in the art will understand that the imager 14 and the sampler 15 may be separate devices or may be a single device performing the functions of both. The collection vessel 17 may be any suitable storage device configured to isolate each tissue sample from other tissue samples and maintain the tissue samples in a suitable condition for testing.

In an exemplary embodiment, the plant handler 13 retrieves the sampled plants from the sampler 15 and transports the sampled plants to a sampled plant location 23. In some embodiments, the sampled plant location 23 may be the entry location 21. In other exemplary embodiments, the imager 14 may determine that the plant may not be suitable for sampling. For example, the imager 14 may communicate with the automatic controls 19 to compare an image of the plant with images of plants suitable for testing. For example, the automatic controls 19 may identify a plant leaf of an imaged plant to have a green hue that is associated with plants that are not healthy. In another embodiment, the automatic controls 19 may identify that an imaged leaf may have a size that is too small for sampling, for example, less than 12 mm×6 mm rectangle. In still another embodiment, the automatic controls 19 may identify that the leaf shape may not be sufficiently rectangular to be suitable for sampling. In response to determining that the plant is unsuitable for sampling, the plant handler 13 may transport the plant from the sampler 15 to an unsuitable plant location 25. In an exemplary embodiment, plants that are not suitable for sampling may be too small or may not yet have reached suitable maturity. These plants may be allowed to further mature or grow before being sampled by the APTSS 11. A person skilled in the art will understand that the sampled plant location 23 and the unsuitable plant location 25 may be the entry location 21. A person skilled in the art will also understand that the automatic controls 19 may include suitable mechanisms, including software, controllers, and the like, configured to identify individual plants relative to the plurality of plants, identify predetermined properties of those plants, and store that information so that the plurality of plants may be maintained in a single location, such as at the entry location 21, of the APTSS 11.

In some embodiments, the plant handler 13, the sampler 15, and the collection vessel 17 are coupled to a frame assembly 29. The frame assembly 29 may be any suitable assembly configured to support the plant handler 13, the imager 14, the sampler 15, and the collection vessel 17 for operation thereof. In an exemplary embodiment, the frame assembly 29 may include a support structure formed of individual members coupled together, one or more components of a location where the APTSS 11 is housed, such as a building floor, foundation, overhead beam, or any suitable support structure.

In the embodiments described herein, the plant or the plurality of plants being sampled may be any suitable plant, for example, corn, soybean, cotton, canola, alfalfa, wheat, sugarcane, rice, or the like. The tissue samples may be taken from any desired location of the plant, for example, from a seed, root, stem, inner stem, stalk or leaf, or the like. For descriptive purposes, a plant of the plurality of plants herein includes any plant parts or plant tissues, which includes tissue cultures. The plants and tissues may or may not be comprised in a growing media. The growing medium may be any suitable substance in which plants or plant tissues may grow or be maintained. A person skilled in the art will understand that the disclosed embodiments include other plants and parts configured in other arrangements.

As shown in FIG. 2, the frame assembly 29 may have a plurality of beams or members coupled together to provide a working frame for the APTSS 11. While the frame assembly 29 is illustrated as a box frame assembly of a plurality of members having a plurality of openings, a person skilled in the art will understand that the frame assembly may be any suitable supportive apparatus or group of apparatuses such that the frame assembly may support the plant handler 13, the imager 14, the sampler 15, and the collection vessel 17 relative to one another for operation of the APTSS 11. In the illustrated embodiment, the frame assembly 29 includes a lower portion 31, a medial portion 33, and an upper portion 35. Lower portion 31, medial portion 33, and upper portion 35 are included herein for reference only and are not intended to limit the embodiments of the frame assembly 29 or the APTSS 11. The frame assembly 29 may have three orthogonal axes, an x-axis 37, a y-axis 39, and a z-axis 41. These axes are presented for descriptive purposes to aid in illustrating the relationships between components of the APTSS 11 and not to limit the embodiments herein. A person skilled in the art will understand that any suitable coordinate reference system may be used to relate the components of the APTSS 11 based on the particular application of the APTSS 11.

Continuing to refer to FIG. 2, the plant handler 13 includes, in one embodiment, a popper assembly or popper 43, a plant receiving area or tray table 45, and an overhead gantry assembly or gantry 47. Popper 37 may be a device movably coupled to the frame assembly 29 in the lower portion 31 of the frame assembly 29 and may be configured to move parallel to the x-axis 37. Referring to FIG. 3, the popper 43 includes, in one embodiment, an actuable member 49 configured to move at least a portion of the popper 43 parallel to the z-axis 41. In the illustrated embodiment, the actuable member 49 may be a pneumatically, hydraulically, mechanically, or electrically operable cylinder configured to move a rod portion 51 parallel to the z-axis 41 toward the medial portion 33 of the frame assembly 29. The automatic controls 19 may be communicatively coupled to the popper 43 to control movement of the popper 43 parallel to the x-axis 37 and control operation of the rod portion 51, i.e. the application of pneumatic, hydraulic, or electric power, to move the rod portion 51 toward the medial portion 33 of the frame assembly 29. In an exemplary embodiment, the rod portion 51 includes an insertive device configured to be inserted into a lower portion of a plant of the plurality of plants to prevent relative motion between the plant and the rod portion 51 when the rod portion 51 engages the plant. A person skilled in the art will recognize that the popper 43 may include one or more controllers, motors, and the like configured to start and stop motion of the popper 43 parallel to the x-axis 37 and the z-axis 41 in response to communicative inputs from, for example, the automatic controls 19. In one exemplary embodiment, the popper 43 may translate about 200 mm parallel to the x-axis 37 and the rod portion 51 may move parallel to the z-axis 41 about 50 mm.

Referring again to FIG. 2, the tray table 45 may be movably coupled to the medial portion 33 of the frame assembly 29 so that the tray table 45 may be generally over the popper 43. The tray table 45 is configured, in one embodiment, to receive the plurality of plants for sampling by the APTSS 11. In the illustrated embodiment, the tray table 45 includes one or more openings configured to receive flats having the plurality of plants. As shown in FIG. 2, the tray table 45 has three openings each of a suitable size and shape to allow placement of a flat 46 in the respective opening. An alternative number of openings in the tray table 45 may be utilized. Each flat 46 has a plurality of openings configured to receive a plant. In the illustrated embodiment, each opening in the flat 46 passes entirely through the flat 46 parallel to the z-axis 41 and accommodates a plug or other growth medium matrix (soil, artificial soil, rockwool, etc.) within each opening. In an exemplary embodiment, the tray table 45 inhibits movement of the flats 46 relative to the tray table 45 along the x-axis 37, the y-axis 39, and the z-axis 41 during operation of the APTSS 11 to ensure that the plants are in a location known by the automatic controls 19 and reachable by the gantry 47.

In the illustrated embodiment, the tray table 45 may receive three flats 46, a first flat 53, a second flat 55, and a third flat 57. The first flat 53 may be a flat 46 containing the plurality of plants to be sampled. The first flat 53 may be delivered by an automatic conveyance system, an operator or laborer, or the like. The first flat 53 may be deposited or placed in one of the openings of the tray table 45. The second flat 55 may be placed in a second opening of the three openings of the tray table 45 and contain no plants when the sampling process begins. In the illustrated embodiment, the second flat 55 may be used to store a plant after the plant has been sampled. The third flat 57 may be placed in a third opening of the tray table 45 and also include no plants when the sampling process begins. In the illustrated embodiment, the third flat 57 may serve as an isolation flat where plants that are not suitable for testing, i.e., the plant may be too small, may be placed for further growth or other treatment. As shown, the first flat 53 may be placed at a first end of the tray table 45 followed by the second flat 55 and the third flat 57 at a second end of the tray table 45. A person skilled in the art will recognize that the flats 53, 55, 57 may be placed in any order provided the placement of each flat 53, 55, 57 is known by the automatic controls 19, and the flat containing the plurality of plants to be sampled is accessible to the popper 43. In some embodiments, each opening of the tray table 45 may receive a first flat 53 to increase the speed of tissue sampling by reducing the interval between plant groups. In these embodiments, the plants may be sampled and returned to their original location in the first flat 53 from which they were selected for sampling. The tray table 45 may be coupled to a plurality of controllers, motors, and the like, and communicatively coupled to the automatic controls 19 so that the tray table 45 may be moved parallel to the y-axis 39.

As shown in FIG. 2, the gantry 47 is movably coupled to the upper portion 35 of the frame assembly 29 so that at least a portion of the gantry 47 is disposed over the tray table 45. In the illustrated embodiment, the gantry 47 includes a plug handler 59 having a plug handler head 61, a first gripper 63, and a second gripper 65. A person skilled in the art will understand that embodiments of the plant handler 13 may have only the first gripper 63. Generally, the gantry 47 is configured to move the plug handler 59 parallel to the x-axis 37 and includes suitable control mechanisms, control wiring, controllers, motors, and the like to accomplish motion. In addition, the automatic controls 19 may be communicatively coupled to the gantry 47 to operate the control mechanisms for operation thereof. The plug handler 59 has a first end proximate to the upper portion 35 of the frame assembly 29 and a second end proximate to the tray table 45. The plug handler head 61 is coupled to the second end of the plug handler 59. In the illustrated embodiment, the plug handler head 61 may be rotatable so that the first gripper 63, and the second gripper 65 may rotate about an axis passing through the plug handler 59 parallel to the z-axis 41. The grippers 63, 65 may be a suitable device configured to grip a plant of the plurality of plants when the plant of the plurality of plants is placed proximate to the grippers 63, 65 by the popper 43. In the illustrated embodiment, the grippers 63, 65 are clamping devices that may be pneumatically, hydraulically, electrically or otherwise actuated to apply a compressive force to the plug of the plant when the plug is placed proximate to the grippers 63, 65.

In an operative embodiment, the APTSS 11 may receive the first flat 53 from any suitable conveyance system 29 (FIG. 1). The automatic controls 19 may operate to move the popper 43, the tray table 45, and the gantry 47 so that the popper 43 is positioned beneath one of the plants of the first flat 53 and the first gripper 63 is positioned above the same plant. The automatic controls 19 may then actuate the actuable member 49 to drive the rod portion 51 upwards toward the plant, engaging the insertive device with the plant. The rod portion 51 may have a sufficient throw to drive the plant from the first flat 53 upwards and adjacent to the first gripper 63. There, the first gripper 63 may be actuated by the automatic controls 19 to close on the plant and secure the plant within the first gripper 63. The rod portion 51 may be retrieved by the actuable member 49, leaving the plant at the elevation of the first gripper 63. In some embodiments, the plug handler 59 may be movable parallel to the z-axis 41 so that the plug handler may be lowered proximate to the tray table 45 to retrieve the plant without the assistance of the popper 43. Once the plant is secured in the first gripper 63, the gantry 47 may be actuated by the automatic controls 19 to move parallel to the x-axis 37 to bring the plug handler 59 and the first gripper 63 proximate to the imager 14 and the sampler 15. A person skilled in the art will recognize that the plant handler 13 may include one or more controllers, motors, and the like configured to start and stop motion of the tray table 45, the gantry 47, the plug handler 59, the first gripper 63, and the second gripper 65 parallel to the x-axis 37, the y-axis 39, and the z-axis 41 in response to communicative inputs from, for example, the automatic controls 19.

In an exemplary embodiment, the plug handler head 61 includes a reader or scanner 67, such as a bar code scanner or camera. The scanner 67 may be any suitable device configured to identify a code, label, tag, object, or other identifier placed on, in proximity to, or incorporated into an individual plant of the plurality of plants. Alternatively, the scanner 67 may be configured to recognize an image or shape of a plant or carrier of the plant. In illustrative embodiments the code or label may be a bar code, a radio frequency identification tag, or any other suitable identifier. The scanner 67 may be communicatively coupled to the automatic controls 19. In the illustrated embodiment, the scanner 67 is positioned so that the a bar code disposed on each flat 46 may be read by the scanner 67. The scanner 67 may communicate this identification information to the automatic controls 19, and the automatic controls 19 may store the identification information of the bar code in an internal or external memory of the automatic controls 19. The size, shape, and number of plants on each flat 46 is also stored in the automatic controls 19. The automatic controls 19 may track each plant based on the plant's position on the flat 46 associated with the scanned bar code for the flat 46. In another exemplary embodiment, the scanner 67 may be coupled to the plug handler head 61 so that a bar code on the plant may be read by the scanner 67 when the plant is secured in the first gripper 63. In yet another exemplary embodiment, each plant may be separately conveyed to the APTSS 11 without a flat 46. Each plant may then also include a bar code or other identifier that may be read by the scanner 67.

In one exemplary embodiment, the identifier associated with each plant may include information relating to the plant type, planting date, germination date, variety, or attribute information. This attribute information could include transgenes conferring resistance to heat, cold, fungi, parasitcs, viruses, bacteria, drought, and the like. The attribute information may also include size, shape, or color at previous samplings. This information may be in a database stored in the identifier or in a separate location in communication with the identifier or scanner 67 so that the information may be accessed by the automatic controls 19 or any other suitable device. In addition, the imager 14 may be in communication with the database so that information relating to the size shape and color of the sampled plant prior to sampling may also be stored and associated with the identifier. A person skilled in the art will understand that the database may include any other suitable information as needed for the particular application of APTSS 11.

The gantry 47 is generally disposed over the entry location 21 and the tray table 45, and includes a portion proximate to the imager 14 and the sampler 15. The gantry 47 may move the plug handler 59 proximate to the imager 14 and the sampler 15, where the plant may be transferred from the first gripper 63 to the sampler 15 as described in more detail below. In an exemplary embodiment, following sampling of the plant, the plant may be transferred back to the plug handler 59 and transported to the second flat 55.

Figure 5:
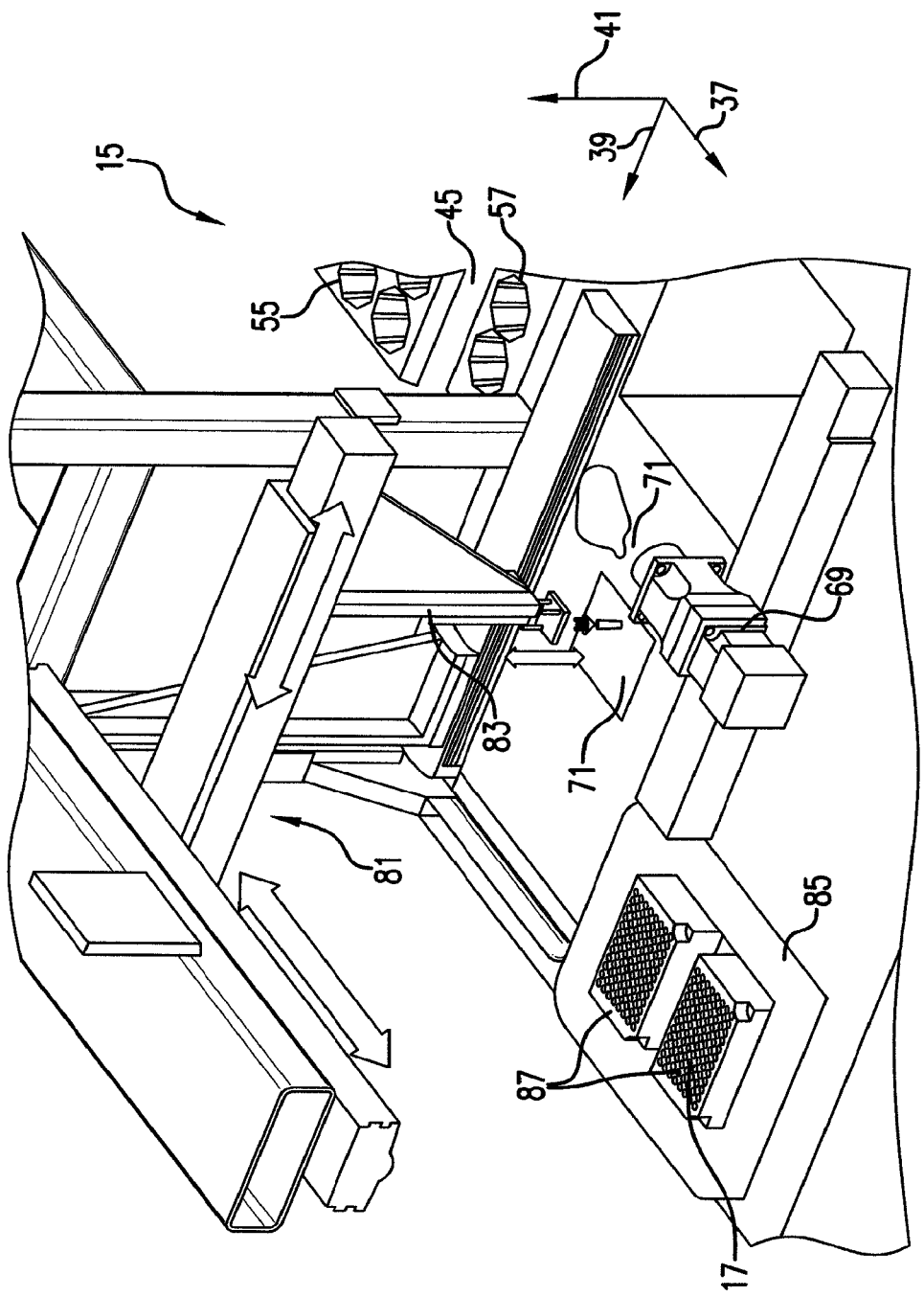
FIG. 5 illustrates a schematic perspective view of the plant sampling portion of the automatic plant tissue sampler of FIG. 2.

Continuing to refer to FIG. 2, the sampler 15 includes a plant positioner 69, a chuck 71, a cutter 75, and a tissue sample transporter (TST) 81. As shown, the imager 14 is proximate to the sampler 15 so that the sampler 15 may be guided by the imager 14 to remove a tissue sample as described in more detail below. As shown in FIG. 5, the plant positioner 69 includes a plant gripper 77. Plant gripper 77 is similar to the first and second grippers 63, 65 of the plant handler 13 and may operate in a similar manner in response to control inputs from the automatic controls 19. In addition, the plant gripper 77 may be rotatable about an axis parallel to the x-axis 37 so that the plant gripped by the plant gripper 77 may be rotated about an axis parallel to the x-axis 37. In addition, the plant positioner 69 is movably coupled to the frame assembly 29 so that the plant positioner 69 may move parallel to the y-axis 39. Rotation of the plant about the axis parallel to the x-axis 37 and translation of the plant parallel to the y-axis 39 permits the plant to be oriented for proper imaging by the imager 14 and sampling by the sampler 15 as described in more detail below. A person skilled in the art will recognize that the plant positioner 69 may include suitable control mechanisms to operate the plant positioner 69 as disclosed herein. A person skilled in the art will recognize that the plant positioner 69, the chuck 71, the cutter 75, and the TST 81, may include one or more controllers, motors, and the like configured to start and stop motion parallel to the x-axis 37, the y-axis 39, and the z-axis 41 in response to communicative inputs from, for example, the automatic controls 19.

Figure 4:
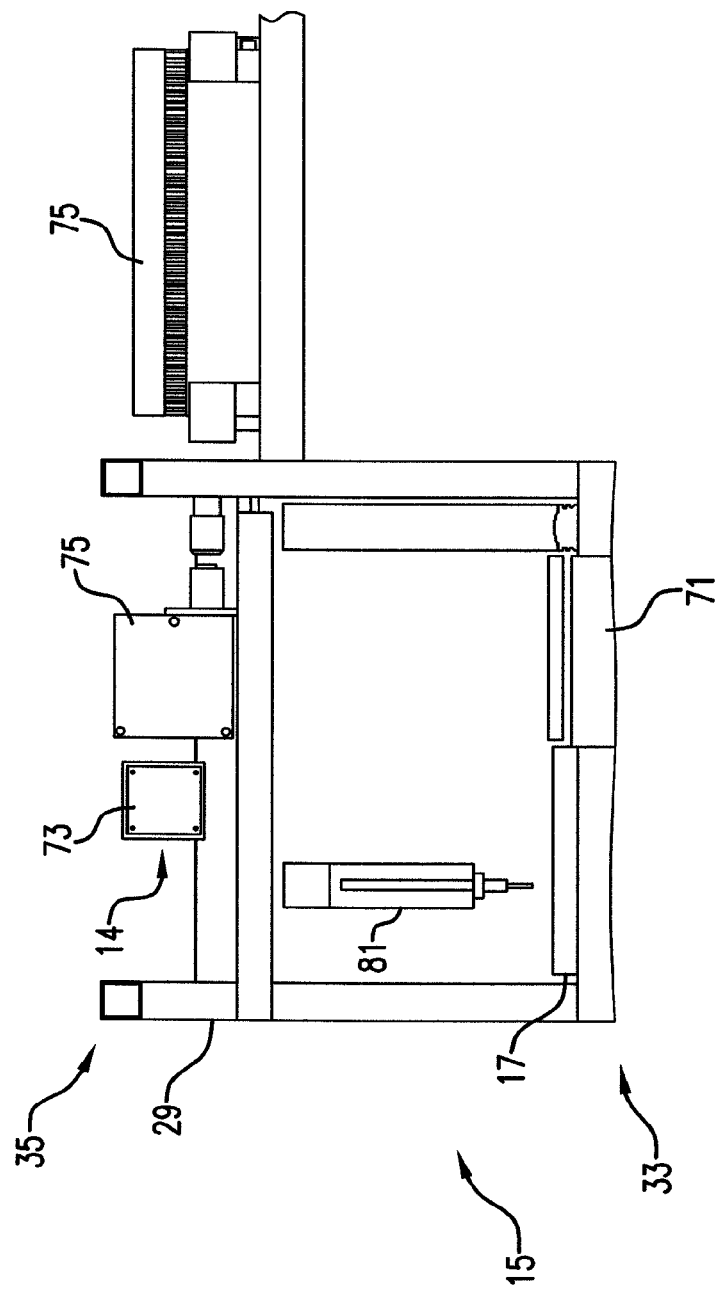
FIG. 4 illustrates a schematic rear elevation view of an illustrative plant sampling portion of the automatic plant tissue sampler of FIG. 2.

Referring to FIG. 4, a partial side elevation view of the imager 14 and the sampler 15 is shown. As shown in FIG. 4, the chuck 71 may be positioned on the medial portion 33 of the frame assembly 29. The cutter 75 may be coupled to the upper portion 35 of the frame assembly 29. In the illustrated embodiment, the cutter 75 may be a laser cutter configured to direct a cutting laser at a surface of the chuck 71. In other embodiments, the cutter 75 may be a plurality of knives configured to cut the tissue sample, a tissue squeezing device configured to apply compressive pressure to remove the tissue sample, or a hole punching device. In the illustrated embodiment, the chuck 71 may be a vacuum chuck supplied with a pressure source adapted to generate a pressure less than the ambient pressure of APTSS 11 above the surface of the chuck 71. The chuck 71 may have a porous platform having a fan positioned relative to the porous platform so that, when operated, the fan may draw a high volume of air through the porous platform. The imager 14 may also be coupled to the upper portion 35 of the frame assembly 29 so that the plant may be exposed to the imager 14 when the plant is proximate to the chuck 71. In the illustrated embodiment, the imager 14 may be an imaging system configured to image the plant and determine one or more of the plant size, shape, or color. The imager 14 may be a visible, infrared, ultraviolet, or any other suitable camera. The plug handler 59 may be brought proximate to the plant positioner 69 and the plug handler head 61 rotated so that the plant may be transferred from the first gripper 63 to the plant positioner 69. In an embodiment, the plant gripper 77 and the first gripper 63 occupy a same horizontal plane so that the transfer may occur by having the plant gripper 77 actuate and secure the plant and the first gripper 63 actuate to release the plant.

The plant positioner 69 may receive the plant from the first gripper 63 and position the plant proximate to the chuck 71 so that the imager 14 may image the plant. In response to the image generated by the plant, the automatic controls 19 may operate the plant positioner 69 to position the sampling location adjacent the surface of the chuck 71. In one exemplary embodiment, the plant positioner 69 orients the plant so that a stem or stalk of the plant is at a forty-five degree angle with the porous platform of the chuck 71. The plant positioner 69 drags or "paints" the plant across the chuck 71 until the imager 14 identifies a tip of a last leaf of the plant. In the illustrated embodiment, the automatic controls 19 include appropriate control mechanisms, software, hardware, etc., to allow the automatic controls 19 to detect the upper-most green section of a leaf. Once detected, the automatic controls 19 then stop movement of the plant positioner 69 so that the tip of the last leaf of the plant is proximate to the chuck 71. The chuck 71, actuated to generate a pressure less than the ambient pressures of the APTSS 11 on the surface of the chuck 71 prior to placement of the tip of the last leaf of the plant proximate to the chuck 71, draws the sampling location into contact with the chuck 71 and immobilizes the sampling location. In an embodiment, the sampling location may be a plant leaf having a suitable size, color, and shape such that removing a portion of the leaf will not irreparably damage the leaf causing death of the leaf or the plant. Once the sampling location is immobilized by the chuck 71, the laser cutter or cutter 75 may be operated to cut a portion of the sampling location from the plant. In an exemplary embodiment, the sampler is guided by the image produced by the imager 14 to cut a tissue sample of a predetermined sized from the sampling location. In one exemplary embodiment, the tissue sample is a rectangle having a length of about 6 mm and a width of about 12 mm. A person skilled in the art will recognize that the size of the tissue sample may vary as needed to accommodate the type of testing to be performed with the tissue sample. A person skilled in the art will also recognize that the embodiments disclosed herein may be modified without changing their general operation to accommodate a wide variety of tissue sample sizes.

Referring again to FIG. 5, following cutting of the tissue sample from the sampling location, the automatic controls 19 may operate the TST 81 to move to the chuck 71, retrieve the tissue sample, and transport the tissue sample to the collection vessel 17. In the illustrated embodiment, the TST 81 may be an assembly mounted to the upper portion 35 of the frame assembly 29 proximate to the chuck 71. The TST 81 may include a pneumatic pick and place device having a member 83 configured to be positioned proximate to the surface of the chuck 71 and supplied with a vacuum pressure of sufficient strength to draw the tissue sample off of the surface of the chuck 71 when the vacuum pressure is applied by the member 83. The member 83 may then be moved along the x-axis 37 and the y-axis 39 to place the tissue sample proximate to the collection vessel 17. A person skilled in the art will understand that TST 81 includes suitable actuators, motors, and pneumatic system devices configured to generate a vacuum pressure in member 83 and translate member 83 relative to the chuck 71 and the collection vessel 17 to move the tissue sample from the chuck 71 to the collection vessel 17. The TST 81 and the sampler 15 may also include suitable devices configured to clean the TST 81 and the sampler 15 following collection of each tissue sample to prevent contamination between samples. The TST 81 can also include an additional bar code scanner to read barcodes associated with the collection vessel 17.

As shown in FIG. 5, the collection vessel 17 includes a storage bin 85 positioned adjacent the sampler 15 so that the TST 81 may place the member 83 axially over the storage bin 85. The collection vessel 17 also includes bodies 87 having a plurality of storage locations. In the illustrated embodiment, the bodies 87 may be microtiter plates each having a plurality of wells or test tubes associated with a separate plant of the plurality of plants on the first flat 53. In an exemplary embodiment, the TST 81 may bring the tissue sample proximate to the bodies 87 and release the vacuum pressure applied to the member 83 to deposit the tissue sample in a particular location or well of the bodies 87, the particular location associated with the particular plant from which the tissue sample was removed. In an exemplary embodiment, the storage bin 85 is packed with dry ice to maintain the tissue samples at a predetermined temperature for storage thereof.

Figure 6:
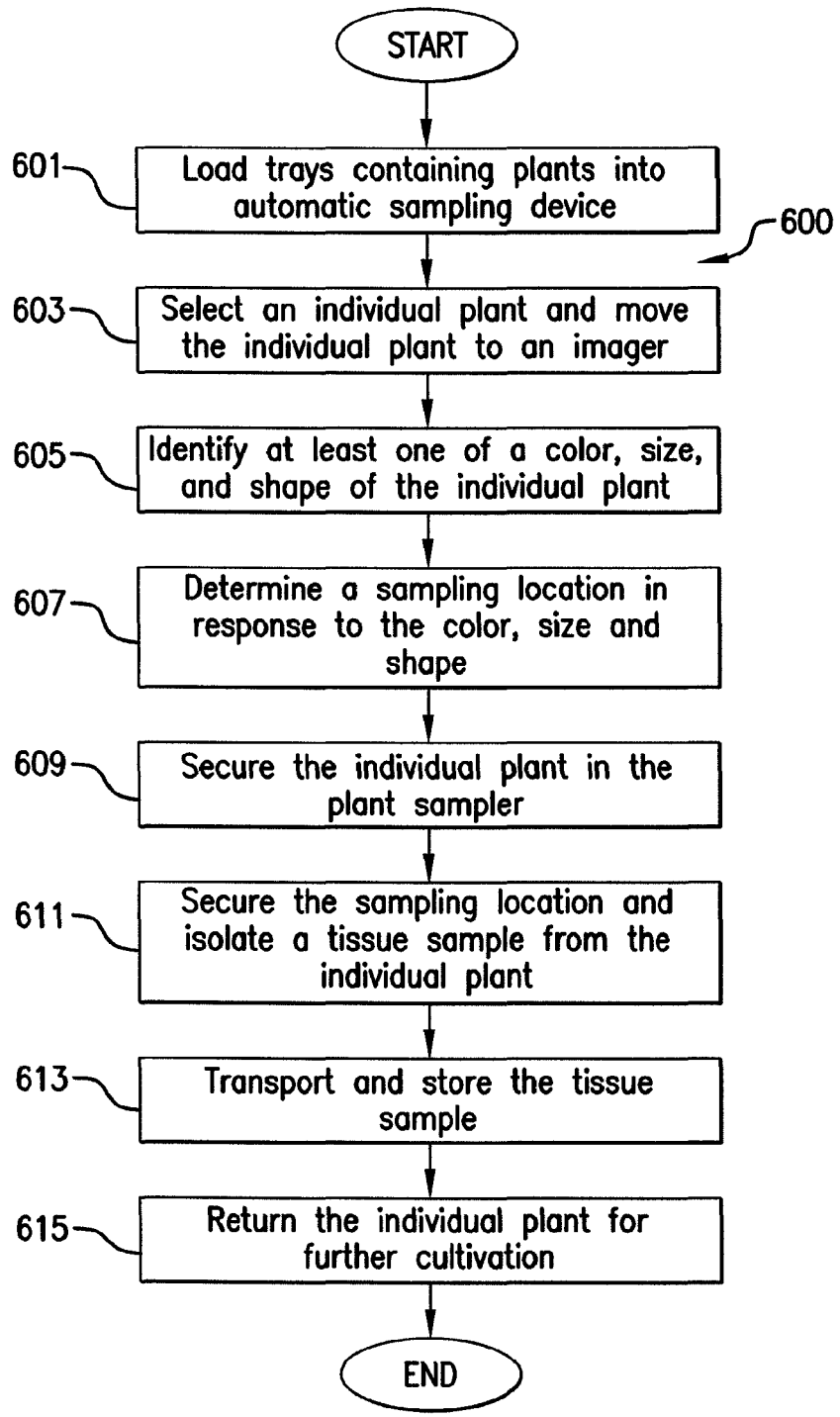
FIG. 6 illustrates a flowchart demonstrating an illustrative process of automatically sampling plant tissue.

FIG. 6 illustrates a high-level flow chart that depicts logical operative steps of the APTSS 11 of FIGS. 1-5, which may be implemented in accordance with an embodiment. As indicated at block 601, the process beings by loading trays containing a plurality of plants into an automatic sampling device. For example, the first flat 53 having the plurality of plants thereon is conveyed into the entry location 21 of the APTSS 11. Next, as indicated at block 603, the APTSS 11 selects an individual plant and moves the individual plant to an imager. For example, the plant handler 13 selects and transports an individual plant on the first flat 53 and transports the plant to the imager 14.

The APTSS 11 identifies at least one of the color, shape, or size of the plant at block 605. For example, the imager 14 of the sampler 15 determines at least one of the plant's color, shape, or size. At block 607, the APTSS 11 determines a sampling location in response to the identification of at least one of the size, shape, and color of the plant. For example, the imager 14 determines the sampling location of the plant in response to previously identified at least one of the size, shape, and color of the plant. Next, as indicated at block 609, the APTSS 11 secures the individual plant in the plant sampler. For example, the plant positioner 69 of the sampler 15 secures the plant within the sampler 15.

At block 611, the individual plant is secured and a tissue sample is isolated from the sampling location. For example, the plant positioner 69 positions the sample location over the chuck 71. The chuck 71 may immobilize the sampling location of the plant with vacuum pressure. The cutter 75 may cut the plant at the sampling location to create a tissue sample. Next, at block 613, the APTSS 11 transports and stores the tissue sample. For example, the TST 81 moves proximate to and applies vacuum pressure to the tissue sample to secure the tissue sample to the member 83 of the TST 81. The TST 81 then transports the tissue sample to the collection vessel 17, where the tissue sample is stored in an isolated location in collection vessel 17 associated with the plant from which the sample was taken. The process ends at block 615, where the individual plant is returned for further cultivation. For example, the plant positioner 69 transfers the plant to the plant handler 13, where the plant is transported to the second flat 55 and deposited in a suitable location therein.

Figure 7:
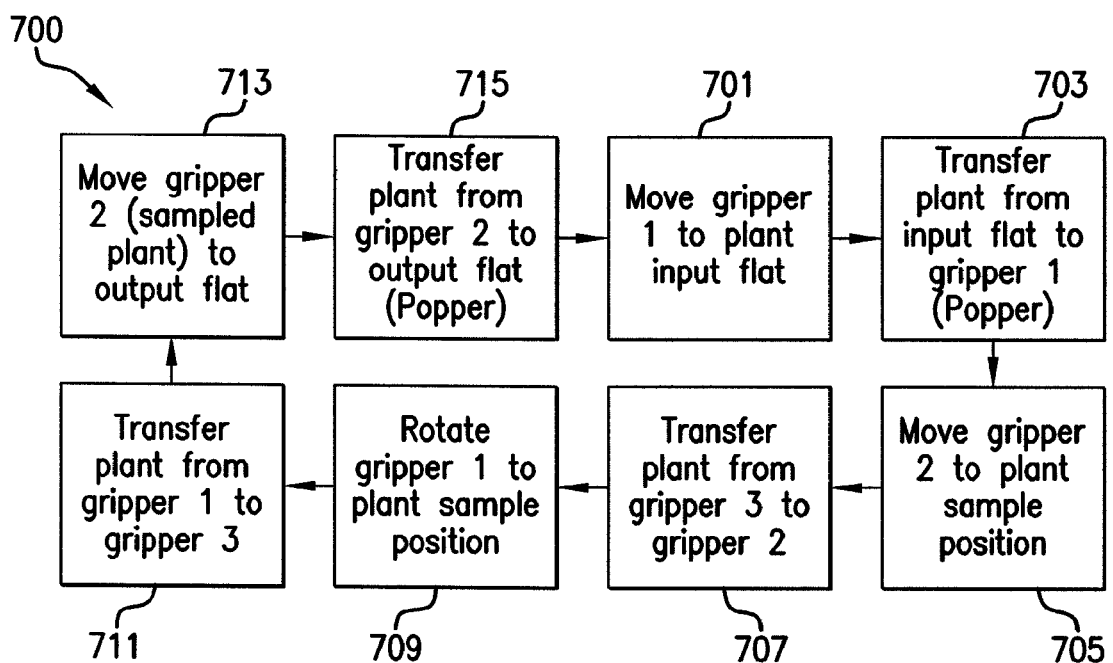
FIG. 7 illustrates a flowchart demonstrating an illustrative process of automatically moving plants for sampling plant tissue.

Referring now to FIG. 7, a high-level flow chart that depicts logical operative steps of the plant handler 13 performed by, for example, plant handler 13 of FIGS. 1-3, which may be implemented in accordance with an embodiment. As indicated at block 701, the process begins by moving a first gripper, gripper one, to the plant input flat. For example, the gantry 47 moves the plug handler 59 to position the first gripper 63 proximate to the first flat 53. Next, as indicated at block 703, the plant handler 13 transfers an un-sampled plant from the input flat to gripper one. For example, the plant handler 13 operates the popper 43 to move the un-sampled plant from the first flat 53 into the first gripper 63, and the first gripper 63 is actuated by the automatic controls 19 to secure the un-sampled plant.

As indicated at block 705, the plant handler 13 moves a second gripper, gripper two, to the sample position. For example, the plant handler 13 operates the gantry 47 to move the plug handler 59 proximate to the imager 14 and the sampler 15 so that the second gripper 65 is proximate to the plant positioner 69 of the sampler 15. Next, as indicated at block 707, a sampled plant is transferred from a third gripper, gripper three, to gripper two. For example, the sampled plant is transferred from the plant gripper 77 of the plant positioner 69 to the second gripper 65. In an embodiment, the plant gripper 77 and the second gripper 65 occupy a same horizontal plane so that the transfer may occur by having the second gripper 65 actuate and secure the sampled plant and the plant gripper 77 actuate to release the sampled plant.

As indicated at block 709, gripper one is rotated to the plant sample position. For example, the plant handler 13 rotates the plug handler head 61 on an axis of the plug handler 59 parallel to the z-axis 41 to position the first gripper 63 proximate to the plant gripper 77 of the plant positioner 69. Next, as indicated at block 711, the plant handler 13 transfers the un-sampled plant from gripper one to gripper three. For example, the first gripper 63 of the plant handler 13 transfers the un-sampled plant from the first gripper 63 to the plant gripper 77 of the plant positioner 69. In an embodiment, the plant gripper 77 and the first gripper 63 occupy a same horizontal plane so that the transfer may occur by having the plant gripper 77 actuate and secure the un-sampled plant and the first gripper 63 actuate to release the un-sampled plant.

Referring to block 713, the plant handler 13 moves gripper two to the output flat. For example, the gantry 47 moves the plug handler 59 to position the second gripper 65 proximate to the second flat 55. As indicated at block 715, the plant handler 13 transfers the sampled plant from gripper two to that which then lowers the sampled plant onto the second flat 55.

Figure 8:
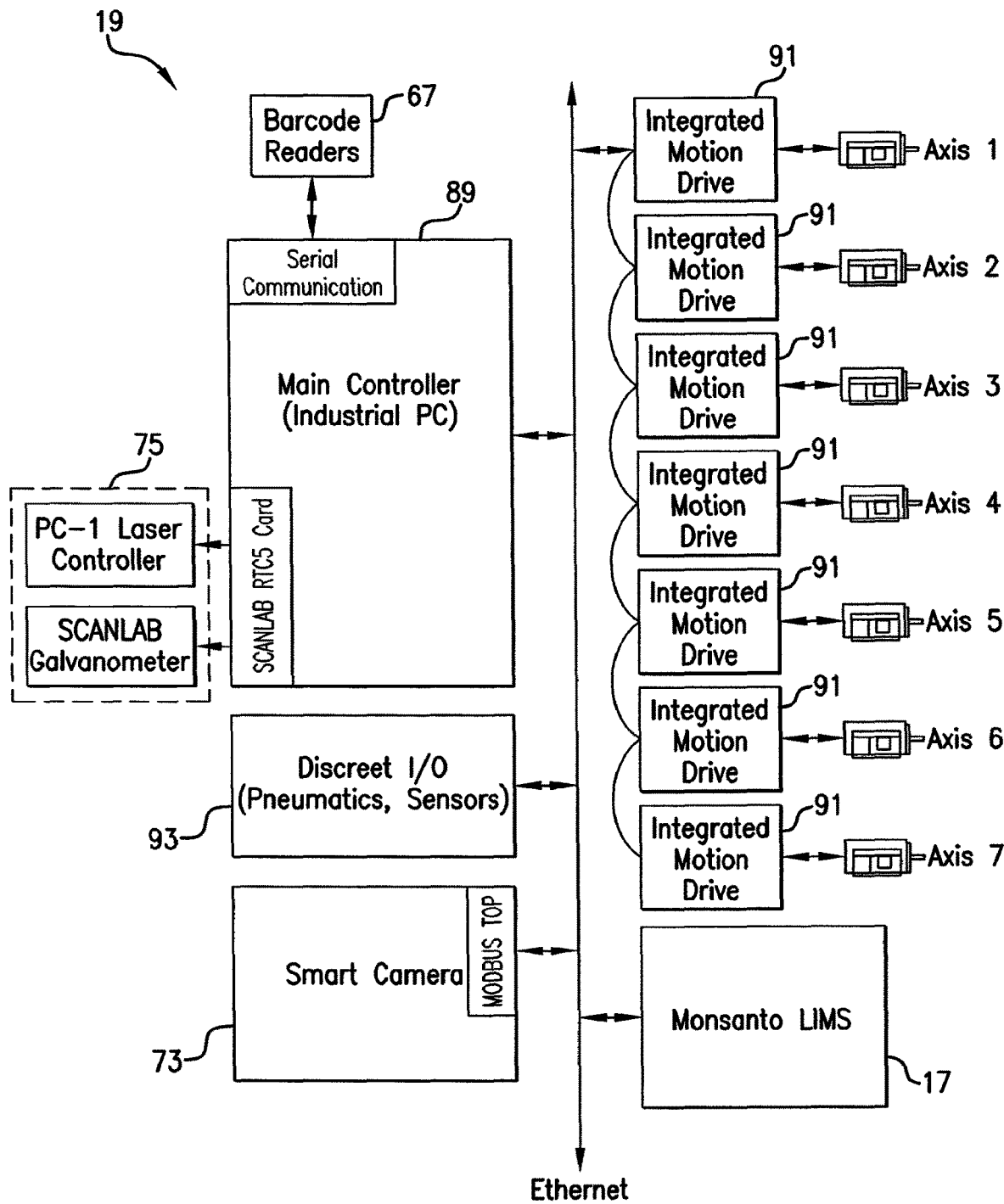
FIG. 8 illustrates a schematic diagram representing exemplary components of an illustrative controls system for automatically sampling plant tissue in accordance with the principles of the present invention.

Referring to FIG. 8, an exemplary embodiment of a portion of the automatic controls 19 is shown. The automatic controls 19 include a main controller 89 that may be communicatively coupled to the scanners 67, the cutter 75, the imager 14, a Monsanto LIMS, a plurality of integrated motion drives 91, and a plurality of discreet input/output devices 93. The main controller 89 may be any suitable computing device or system, such as a programmable logic controller, a data processing system, or the like, configured to receive input from the above listed devices and communicate with those same devices for operation thereof. A data processing system suitable for storing and/or executing program code will include at least one processor coupled directly or indirectly to memory elements through a system bus. The memory elements can include local memory employed during actual execution of the program code, bulk storage, and cache memories, which provide temporary storage of at least some program code in order to reduce the number of times code is retrieved from bulk storage during execution.

The plurality of integrated motion drives 91 are devices configured to move a member parallel to one of the x-axis 37, the y-axis 39, the z-axis 41, a first axis of rotation, a second axis of rotation, or a combination thereof. For example, the plurality of integrated motion drives 91 may be coupled to the elements of the plant handler 13 to move the tray table 45, the popper 43, the gantry 47, the plant positioner 69, and the TST 81. The integrated motion drives 91 are any suitable device configured to receive operative signals or instructions from the main controller 89 and translate or cause the translation of an associated component of the APTSS 11 as described herein.

The discreet input/output devices 93 may be any suitable devices such as pneumatic sensors, temperature sensors, or the like configured to communicate signals to the main controller 89. Input/output or I/O devices (including but not limited to keyboards, displays, pointing devices, etc.) can be coupled to the system either directly or through intervening I/O controllers. Network adapters may also be coupled to the system to enable the automatic controls 19 to become coupled to other data processing systems or remote printers or storage devices through intervening private or public networks. Modems, cable modems, and Ethernet cards are just a few of the currently available types of network adapters.

The disclosed embodiments may be used for collecting tissue samples from most any plant species for analytical testing that could be DNA, RNA, protein, or any other analytical test. The disclosed embodiments may be used on transgenic tissue culture regenerants (R0 plants) or subsequent generations of transgenic plants (R1 and beyond). The disclosed embodiments may also be used to collect samples from non-transgenic plants, for example for the purpose of performing molecular marker analyses in the context of molecular breeding programs, or for testing for metabolites in chemical screens or physiology assays.

It is understood that the present invention may take many forms and embodiments. Accordingly, several variations may be made in the foregoing without departing from the spirit or scope of the invention. Having thus described the present invention by reference to certain of its preferred embodiments, it is noted that the embodiments disclosed are illustrative rather than limiting in nature and that a wide range of variations, modifications, changes, and substitutions are contemplated in the foregoing disclosure and, in some instances, some features of the present invention may be employed without a corresponding use of the other features. Many such variations and modifications may be considered obvious and desirable by those skilled in the art based upon a review of the foregoing description of preferred embodiments. Accordingly, it is appropriate that the appended claims be construed broadly and in a manner consistent with the scope of the invention.

In the description and tables, a number of terms are used. In order to provide a clear and consistent understanding of the specification and claims, the following definitions are provided:

A: When used in conjunction with the word "comprising" or other open language in the claims, the words "a" and "an" denote "one or more."

Or: Unless otherwise indicated, as used throughout this document, "or" does not require mutual exclusivity.

Regeneration: The development of a plant from tissue culture.

Substantially Equivalent: A characteristic that, when compared, does not show a statistically significant difference (e.g., p=0.05) from the mean.

Tissue Culture: A composition comprising isolated cells of the same or a different type or a collection of such cells organized into parts of a plant.

Transgene: A genetic locus comprising a sequence that has been introduced into the genome of a plant by transformation.

It should be apparent from the foregoing that an invention having significant advantages has been provided. While the invention is shown in only a few of its forms, it is not just limited but is susceptible to various changes and modifications without departing from the spirit thereof.

What is claimed is:

1. An apparatus for selecting, sampling, and storing a tissue sample from an individual plant of a group of one or more plants, the apparatus comprising:
   a frame assembly having a first axis, a second axis orthogonal to the first axis, and a third axis orthogonal to the first axis and the second axis;
   a plant handler mounted to the frame assembly and having a plurality of grippers to manipulate the individual plant of the one or more plants to collect a tissue sample of the individual plant;
   a sampler mounted to the frame assembly and having a sample identifier and a tissue sample collection device to identify, collect, and store the tissue sample of the individual plant, the plant handler configured to orient the plant within the sampler; and
   a controls system communicatively coupled to the plant handler and the sampler, the controls system configured to coordinate movement and operation of the plant handler and the sampler.

2. The automatic plant handling apparatus of claim 1, wherein the plant handler comprises:
   a plug handler having one or more of the plurality of grippers, the plug handler mechanically coupled to the frame assembly and configured to move parallel to the first axis between the one or more plants and the sampler, the plug handler further configured to identify the individual plant of the one or more plants and grip the individual plant with one or more of the plurality of grippers for movement of the individual plant relative to the one or more plants;
   a tray table mechanically coupled to the frame assembly, the tray table configured to collectively receive the one or more plants and move relative the frame assembly parallel to the second axis;
   a popper mechanically coupled to the frame assembly and configured to move relative to the frame assembly parallel to the first axis and the third axis; and
   wherein the tray table receives the one or more plants and the controls system operates to move the tray table, the popper, and the plug handler proximate to the individual plant of the one or more plants, the popper engages the individual plant to move the plant along the third axis into a gripper of the plurality of grippers which grips the individual plant and moves along the first axis to transport the individual plant to the sampler.

3. The automatic plant handling apparatus of claim 2, wherein the plug handler further comprises:
- a plug handler head coupled to an end of the plug handler proximate to the tray table;
- the one or more grippers mounted to the plug handler head;
- the plug handler head rotatable to selectively position each gripper of the plurality of grippers in a plan containing the first axis; and
- an identification device coupled to the plug handler head and configured to identify the individual plant, wherein:
- each plant of the one or more plants is labeled with a bar code and the plant identification device comprises a bar code scanner configured to scan the bar code positioned on each individual plant of the one or more plants; or
- wherein each plant of the one or more plants is labeled with a radio frequency identification (RFID) tag and the plant identification device comprises an RFID scanner configured to scan the RFID tag positioned on each individual plant of the one or more plants.

4. The automatic plant sampling apparatus of claim 1, wherein:
the plant handler further comprises:
- a plant positioner having a motorized rotary gripper coupled to the frame assembly and configured to move parallel to the second axis and receive the individual plant from the plant handler;
- a chuck coupled to the frame assembly proximate to the plant positioner, the chuck configured to engage a portion of the individual plant for sampling;

the sampler comprises:
- a imager coupled to the frame assembly proximate to the chuck, the imager configured to determine one or more of the color, shape, and size of the individual plant;
- a cutter coupled to the frame assembly proximate to the chuck, the cutter configured to remove a tissue sample from the sampling location of the individual plant;
- a tissue sample transporter coupled to the frame assembly proximate to the chuck and configured to retrieve the tissue sample of the individual plant from the chuck and transport the tissue sample to a storage assembly;

the plant positioner further configured to manipulate the individual plant to allow the imager to determine one or more of the color, shape, and size of the individual plant and determine the sampling location, the plant positioner positioning the individual plant to align the sampling location with the chuck; and wherein the controls system is communicatively coupled to the plant positioner, the chuck, the imager, the cutter, and the tissue sample transporter to control and operate the plant positioner to manipulate the individual plant for identification by the imager and position the plant so that the sample location is proximate to the chuck, the control system further configured to operate the chuck to secure the sample location to the chuck, operate the sampler to remove the tissue sample from the sampling location, and operate the tissue sample transporter to transport the tissue sample to the storage assembly.

5. The automatic plant sampling apparatus of claim 4, wherein the chuck comprises a vacuum chuck configured to supply a pressure less than an ambient pressure at a location proximate to a surface of the chuck, wherein when the plant positioner brings the sampling location proximate to the chuck, the pressure draws the sample location to the chuck wherein the pressure flattens a portion of the sample location; or
wherein the imager comprises an imaging system having at least one camera.

6. The automatic plant sampling apparatus of claim 4, wherein the sampler comprises:
(i) a laser cutting device;
(ii) a device having a plurality of knives configured to cut the tissue sample from the sample location; or
(iii) a hole punching device configured to apply compressive pressure to remove the tissue sample from the sample location; or
wherein the collection vessel comprises a microtiter having a plurality of isolated locations each location having a scannable label associated with the individual plant and a dry ice receptacle for placing dry ice proximate to the microtiter to maintain the microtiter at a pre-determined temperature.

7. A method for automatically sampling individual plants from a group of one or more plants, the method comprising:
(a) loading flats containing a plurality of plants into an automatic sampling device having a plant handling system and a plant sampling system, each plant having a unique identifier;
(b) selecting an individual plant from the tray and securing the individual plant in the plant handling system;
(c) moving the individual plant with the plant handling system to the plant sampling system;
(d) securing the individual plant with the plant sampling system and releasing the individual plant with the plant handling system;
(e) identifying at least one of a color, size, and shape of the individual plant with the plant sampling system;
(f) determining a sampling location of the individual plant based on at least one of the color, size, and shape of the individual plant;
(g) securing the individual plant for sampling with the plant sampling system;
(h) isolating a tissue sample from the individual plant with the plant sampling system;
(i) transporting the tissue sample to a collection vessel with the plant sampling system and associating the tissue sample with the identifier of the individual plant; and
(j) storing the tissue sample for testing and returning the individual plant for further cultivation with the plant handling system.

8. The method of claim 7, wherein:
step (b) comprises engaging the individual plant with a popper of the plant handling system to move the individual plant from a tray table of the plant handling system into a gripper of the plant handling system, or
wherein step (e) comprises imaging the individual plant with an imaging system of the plant sampling system; or
wherein in response to the determination of shape, size, and color of the individual plant, step (f) comprises selecting the sampling location based on a predetermined size, color, and shape that corresponds with desired characteristics comprising a size, color, and shape associated with an increased likelihood of plant survival; or
wherein step (g) comprises orienting the individual plant so that the sample location is proximate to a chuck of the plant sampling system; positioning the sample location with the chuck so that the sample location is disposed for isolating; and inhibiting movement of the sample location with the chuck; or wherein step (h) comprises cutting the sample location with a laser cutting apparatus to remove the tissue sample from the individual plant; or wherein step (i) comprises collecting the tissue sample with a vacuum system and carrying the tissue sample to a tissue sample collection plate associated with the individual plant.

9. The method of claim 8, wherein step (g) further comprises applying a pressure lower than an ambient pressure of the plant sampling system to draw the sample location to the chuck.

10. The method of claim 7, further comprising, repeating steps (b)-(j) until each individual plant of the plurality of plants is sampled.

* * * * *